United States Patent [19]

Kono et al.

[11] Patent Number: 5,057,615
[45] Date of Patent: Oct. 15, 1991

[54] PROCESS FOR PURIFYING TRYPTOPHAN

[75] Inventors: Yoshitsugu Kono; Hiroyuki Itoh; Ryoichi Taneda; Tsugio Watanabe, all of Omuta, Japan

[73] Assignee: Mitsui Toatsu Chamicals, Inc., Tokyo, Japan

[21] Appl. No.: 544,227

[22] Filed: Jun. 26, 1990

[30] Foreign Application Priority Data

Jun. 27, 1989 [JP] Japan ................................ 1-162688

[51] Int. Cl.$^5$ ............................................ C07D 209/20
[52] U.S. Cl. ................................................ 548/497
[58] Field of Search ........................................ 548/497

[56] References Cited

FOREIGN PATENT DOCUMENTS 0004168 1/1985 Japan .................................. 548/497
0013758 1/1985 Japan .................................. 548/497

OTHER PUBLICATIONS

Patent Abstracts of Japan, Unexamined Applications, C Field, vol. 10, No. 314, Oct. 24, 1986, p. 118 C 380 (Kokai No. 61-126070).
Patent Abstracts of Japan, Unexamined Applications, C Field, vol. 8, No. 130, Jun. 16, 1984, p. 7 C 229 (Kokai No. 59-39857).

Primary Examiner—David B. Springer
Attorney, Agent, or Firm—Burns, Doane, Swecker & Mathis

[57] ABSTRACT

A process for purifying tryptophan is disclosed. In the process of the present invention, tryptophan is recrystallized in water-containing acetic acid. By the process of the present invention, tryptophan with high purity may be obtained with high yield without condensation or neutralization.

3 Claims, 2 Drawing Sheets

PROCESS FOR PURIFYING TRYPTOPHAN

BACKGROUND OF THE INVENTION

1. Field of the Invention

This invention relates to a process for purifying tryptophan.

2. Description of the Related Art

Tryptophan is conventionally obtained from a fermentation liquid or an enzyme reaction product by condensation or by neutralization after cooling and subsequent liquid-solid separation. However, by this conventional method, impurities in the fermentation liquid or in the enzyme reaction product are taken into the crystals of tryptophan, so that it is impossible to obtain tryptophan of high purity.

A method in which tryptophan is recrystallized in the presence of a lower alcohol or a ketone is disclosed in Japanese Laid Open Patent Application (Kokai) No. 39857/84. However, with this method, tryptophan having satisfactory high purity cannot be obtained.

Japanese Laid Open Patent Application No. 126070/86 discloses a method of purifying tryptophan, in which a non-polar porous resin is used. However, in this method, an expensive resin is required. Moreover, the obtained tryptophan solution is very dilute, so that a substantial amount of energy is required for its condensation. Thus, this method is not economical.

In general, to obtain tryptophan with high purity, condensation, recrystallization and solid-liquid separation are required after once dissolving tryptophan so as to remove insoluble impurities. However, since the solubility of tryptophan in water or alcohol is small, a large amount of solvent is required for dissolving tryptophan, so that a large amount of energy is required for the condensation. Moreover, during the condensation, tryptophan is decomposed, so that the purity and yield of tryptophan are reduced.

SUMMARY OF THE INVENTION

Accordingly, an object of the present invention is to provide a process for purifying tryptophan by which the above-mentioned problems are solved and by which tryptophan may be highly purified in an economical and simple way on an industrial scale.

The present inventors intensively studied to find surprisingly that although tryptophan is decomposed by heating in acetic acid, if the acetic acid contains water, the stability of tryptophan is largely promoted.

That is, the present invention provides a process for purifying tryptophan comprising the step of recrystallizing tryptophan in water-containing acetic acid.

By the process of the present invention, purification of tryptophan may be carried out at a high concentration, so that condensation and neutralization are not required. Thus, by the process of the present invention, tryptophan with high purity may be obtained simply and economically with high yields.

DETAILED DESCRIPTION OF THE PREFERRED EMBODIMENTS

The tryptophan which is subjected to the process of the present invention may be crude tryptophan which is prepared by fermentation, enzyme reaction or by chemical synthesis. The tryptophan may have either L- or D-configuration or may be racemic. It should be noted that when only one of L- and D-tryptophan is subjected to the process of the present invention, racemization of the tryptophan does not occur.

In the process of the present invention, the crude tryptophan is recrystallized in water-containing acetic acid. The content of water in the acetic acid may be 1–95% by weight, preferably 2–90% by weight, more preferably 10–80% by weight.

The amount of the water-containing acetic acid may preferably be not smaller than equimolar of the tryptophan in terms of the amount of acetic acid. It should be noted, however, if the amount of the water-containing acetic acid is too much, the yield may be reduced. Thus, the amount of the water-containing acetic acid may preferably be 3 to 200 times that of the number of moles of tryptophan in terms of the number of moles of acetic acid.

The temperature employed in the recrystallization step may be any temperature as long as tryptophan can be completely dissolved in the water-containing acetic acid. Usually, the temperature is preferably 40° to 115 °C.

To the heated solution in which tryptophan is dissolved, if necessary, active carbon or a filter aid may be added so as to adsorb impurities or to aid the filtering off of the insoluble materials. The active carbon may be one generally employed for the purification by recrystallization. Preferred examples of the filter aid may include active carbon, diatomaceous earth, bentonite, acidic terra alba and talc.

The recrystallization step per se may be carried out in a manner similar to conventional methods by cooling a solution of tryptophan in water-containing acetic acid. To effectively obtain tryptophan crystals, the tryptophan solution may usually be cooled to 40°–0° C., preferably 20°–5° C.

The obtained crystals of tryptophan may be recovered by filtration, washed with aqueous acetic acid solution or cold water, and dried in a conventional manner in atmospheric or reduced pressure to obtain highly purified tryptophan. It should be noted that in the process of the present invention, neutralization with an alkali is not required and the acetic acid may be recovered from the filtrate by distillation or the like.

Figure 1:
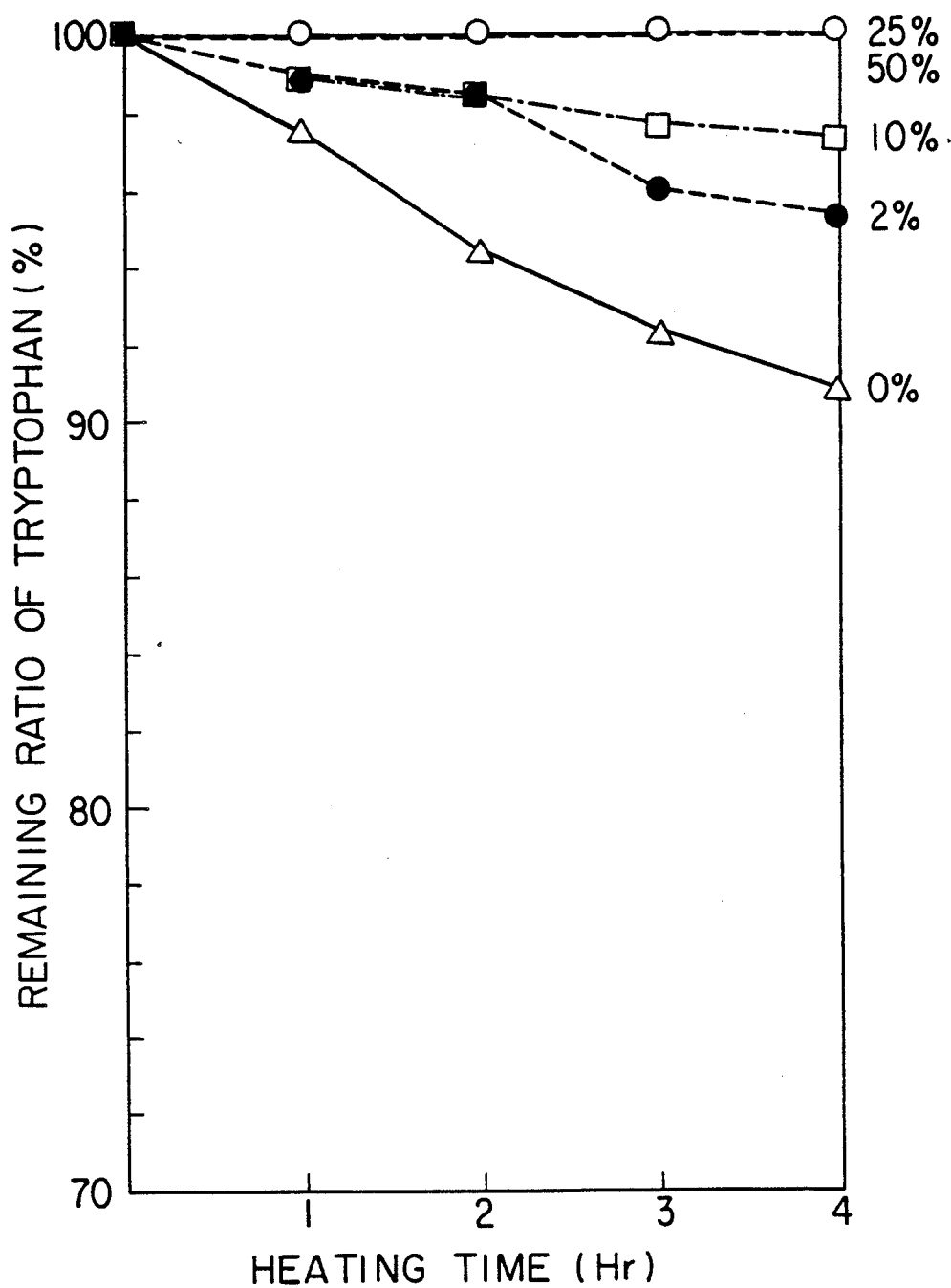
FIG. 1 shows the stability of tryptophan in acetic acid containing various amounts of water.

FIG. 1 shows the stability of tryptophan in acetic acid containing various amounts of water. In FIG. 1, the abscissa indicates the time period of heating and the ordinate indicates the ratio of the remaining tryptophan. Further, the figures accompanying "%" mean the water content in the acetic acid. The heat treatment was conducted at 90° C. As can be seen from FIG. 1, addition of water to acetic acid largely promote the stability of tryptophan. Because of the large stability of tryptophan in the water-containing acetic acid, tryptophan is not substantially thermally decomposed during the recrystallization step.

Figure 2:
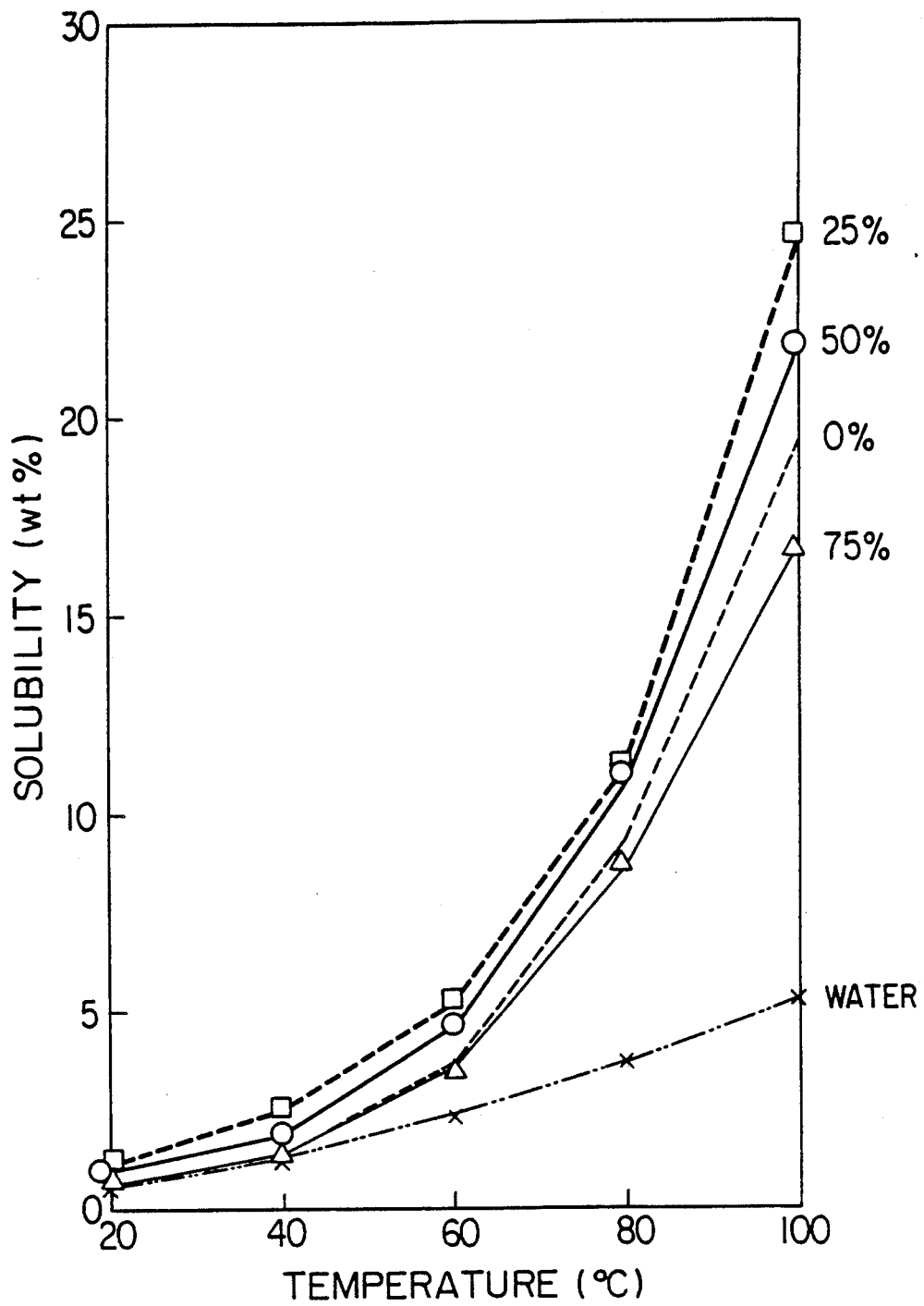
FIG. 2 shows solubility of tryptophan at various temperatures in acetic acid containing various amounts of water or in water.

Further, tryptophan has large solubility in the water-containing acetic acid. FIG. 2 shows the solubility of tryptophan at different temperatures in water or in acetic acid containing various amounts of water. In FIG. 2, the abscissa indicates the temperature and the ordinate indicates the solubility of tryptophan. The figures accompanying "%" mean the water content in the acetic acid. As can be seen from FIG. 2, tryptophan has large solubility in the acetic acid with wide range of water content. This clearly supports the conclusion that water-containing acetic acid is an excellent solvent for purification of tryptophan. That is, since tryptophan has large solubility in the water-containing acetic acid, the recrystallization step may be carried out at a high concentration of tryptophan, so that the condensation step which was inevitable in the conventional process is not necessary.

The present invention will now be described in more detail by way of examples thereof. It should be understood that the examples are presented for the illustration purpose only and should not be interpreted in any restrictive way.

EXAMPLE 1

Indole and serine were condensed in an aqueous solution in the presence of tryptophan synthase produced by culturing a conventional *E. coli* to obtain a reaction product containing 15% by weight of L-tryptophan. To 200 g of the thus obtained reaction product, 140 g of acetic acid was added and the mixture was heated to 90° C. To the resultant mixture, 0.3 g of active carbon was added and the resulting mixture was heated at this temperature for another one hour. After removing insoluble materials by filtration, the filtrate was cooled to 20° C. and was kept at this temperature for one hour. The generated crystals were recovered by filtration. The recovered crystals were washed with 60 g of cold water and was dried in a dryer to obtain 27 g of L-tryptophan. The yield from the reaction product was 89.0%, and the purity of the obtained tryptophan was 98.9%.

COMPARATIVE EXAMPLE

Two hundred grams of the reaction product containing 15% by weight of L-tryptophan obtained in Example 1 was filtered as it was and was washed with 60 g of cold water. By drying the filtrate, 29 g of L-tryptophan was obtained. The yield from the reaction product was 90.3% and the purity of the obtained tryptophan was 93.4%.

EXAMPLE 2

To a mixed solvent consisting of 70 g of acetic acid and 70 g of water, 25 g of the crude L-tryptophan obtained in Comparative Example was added and the resulting mixture was heated at 90° C. To the resultant mixture, 0.2 g of active carbon was added and the resulting mixture was heated at 90° C. for one hour. The insoluble materials were removed by filtration and the filtrate was cooled to 20° C. After maintaining the filtrate at this temperature, the generated crystals were recovered by filtration. The recovered crystals were washed with 50 g of cold water and was dried in a dryer to obtain 22 g of tryptophan. The yield was 93.4% and the purity of the obtained tryptophan was 99.1%.

Although the invention was described by way of a preferred embodiment thereof, it is apparent for those skilled in the art that various modifications may be made without departing from the scope and spirit of the present invention. Thus, the scope of the present invention should be determined by the appended claims.

We claim:

1. A process for purifying tryptophan without involving neutralization with an alkali, said process comprising the steps of dissolving tryptophan in water-containing acetic acid and the presence of heat and cooling the resulting tryptophan solution to obtain recrystallized tryptophan.

2. The process of claim 1, wherein said water-containing acetic acid contains 10–80% by weight of water, said water-containing acetic acid is used in the amount of 3 to 200 times that of the number of moles of tryptophan in terms of the number of moles of said acetic acid, said step of dissolving tryptophan is carried out at a temperature between 40°–115° C., and wherein the tryptophan solution is cooled to a temperature between 5°–20° C. in said step of cooling said tryptophan solution.

3. The process of claim 2, further comprising the steps of adding a substance selected from the group consisting of active carbon, diatomaceous earth, bentonite, acidic terra alba or talc to the solution of tryptophan after the tryptophan is dissolved, and then removing the added substance by filtration.

* * * * *